(12) United States Patent
Tang et al.

(10) Patent No.: US 8,722,131 B2
(45) Date of Patent: May 13, 2014

(54) COMESTIBLE EMULSIONS

(75) Inventors: Dongming Tang, Dartmouth (CA); Sylvie Cloutier, Dartmouth (CA)

(73) Assignee: DSM Nutritional Products AG, Kaiseraugst (CH)

( * ) Notice: Subject to any disclaimer, the term of this patent is extended or adjusted under 35 U.S.C. 154(b) by 112 days.

(21) Appl. No.: 13/226,927

(22) Filed: Sep. 7, 2011

(65) Prior Publication Data

US 2012/0058241 A1 Mar. 8, 2012

Related U.S. Application Data

(60) Provisional application No. 61/380,577, filed on Sep. 7, 2010.

(51) Int. Cl.
*A23L 1/035* (2006.01)

(52) U.S. Cl.
USPC ........... 426/604; 426/601; 426/602; 426/612; 426/590

(58) Field of Classification Search
CPC ......... A23L 2/60; A23L 1/3008; A23L 1/035; A23V 2250/712; A23V 2250/628
USPC .......................... 426/601, 602, 604, 612, 590
See application file for complete search history.

(56) References Cited

U.S. PATENT DOCUMENTS

| | | | |
|---|---|---|---|
| 2,167,144 A * | 7/1939 | Barton et al. | 424/554 |
| 2,680,749 A | 12/1951 | Cawley et al. | |
| 3,102,078 A | 8/1963 | Robeson | |
| 4,005,196 A | 1/1977 | Jandacek et al. | |
| 4,963,380 A | 10/1990 | Schroeder et al. | |
| 5,532,002 A | 7/1996 | Story | |
| 5,583,105 A | 12/1996 | Kovacs et al. | |
| 5,650,157 A | 7/1997 | Bockow | |
| 5,738,871 A | 4/1998 | Story | |
| 5,753,241 A | 5/1998 | Ribier et al. | |
| 5,776,978 A | 7/1998 | Bruzzese | |
| 5,798,333 A | 8/1998 | Sherman | |
| 5,976,606 A | 11/1999 | Koga et al. | |
| 6,039,936 A | 3/2000 | Restle et al. | |
| 6,159,507 A | 12/2000 | Igarashi | |
| 6,235,331 B1 | 5/2001 | Kataoka et al. | |
| 7,118,688 B2 | 10/2006 | Mora-Gutierrez et al. | |
| 7,402,327 B2 | 7/2008 | Zhong et al. | |
| 7,431,986 B2 | 10/2008 | Van Lengerich et al. | |
| 2004/0131727 A1 | 7/2004 | Nakajima et al. | |
| 2004/0146551 A1 | 7/2004 | Mannino et al. | |
| 2006/0134178 A1 | 6/2006 | Doisaki et al. | |
| 2006/0178351 A1 | 8/2006 | Curd et al. | |
| 2007/0071876 A1 | 3/2007 | Smorholm | |
| 2007/0098787 A1 | 5/2007 | Kakiuchi | |
| 2007/0098854 A1 | 5/2007 | Van Lengerich et al. | |
| 2007/0104849 A1 | 5/2007 | McClements et al. | |
| 2007/0141203 A1 | 6/2007 | Cook | |
| 2007/0184117 A1 | 8/2007 | Gregory et al. | |
| 2007/0189977 A1 | 8/2007 | Zhang et al. | |
| 2007/0298083 A1 | 12/2007 | Mehansho et al. | |
| 2007/0299133 A1 | 12/2007 | Mehansho et al. | |
| 2008/0138493 A1 | 6/2008 | Van Seeventer et al. | |
| 2008/0199589 A1 | 8/2008 | Patist et al. | |
| 2008/0200546 A1 | 8/2008 | Casey et al. | |
| 2008/0274195 A1 | 11/2008 | Nicolosi et al. | |
| 2009/0001774 A1 | 1/2009 | Hahn et al. | |
| 2009/0001775 A1 | 1/2009 | Smith | |
| 2009/0018186 A1 | 1/2009 | Chen et al. | |
| 2009/0029017 A1 | 1/2009 | Singh et al. | |
| 2009/0061048 A1 | 3/2009 | Kohane et al. | |
| 2009/0297665 A1 * | 12/2009 | Bromley | 426/72 |
| 2010/0104730 A1 | 4/2010 | Mehansho et al. | |
| 2010/0323066 A1 | 12/2010 | Comstock | |
| 2011/0118351 A1 | 5/2011 | Berl | |

FOREIGN PATENT DOCUMENTS

| | | |
|---|---|---|
| CN | 101259101 A | 9/2008 |
| CN | 101259102 A | 9/2008 |
| DE | 102007057258 A1 | 6/2009 |
| EP | 2359698 A1 | 8/2011 |
| GB | 2444896 A | 6/2008 |
| WO | 2006009825 | 1/2006 |
| WO | WO2006009825 | 1/2006 |
| WO | 2008/039564 A1 | 4/2008 |
| WO | 2009/078245 A1 | 6/2009 |
| WO | 2009117151 | 9/2009 |
| WO | 2009117152 | 9/2009 |
| WO | 2010/008762 A1 | 1/2010 |
| WO | 2010/035704 A1 | 4/2010 |
| WO | 2010/091853 A2 | 8/2010 |
| WO | 2011/119228 A1 | 9/2011 |
| WO | 2010/008762 * | 11/2013 |

OTHER PUBLICATIONS

Supplementary International Search Report for Application No. PCT/IB2011/002743 dated Jul. 9, 2012.
International Search Report and Written Opinion for Application No. PCT/IB2011/002743 dated Mar. 9, 2012.
Dyrberg et al., In: Omega-3 Fatty Acids: Prevention and Treatment of Vascular Disease, Kristensen et al., eds., Bi & Gi Publ., Verona-Springer-Verlag, London, pp. 217-226 (1995).
Griffin, W.C., Classification of Surface-Active Agents by HLB, Journal of the Society of Cosmetic Chemists, 1: 311 (1949).
Harris, Extending the cardiovascular benefits of omega-3 fatty acids, Curr. Atheroscler. Rep., 7:375-380 (2005).
Hogan et al., Microencapsulation and oxidative stability of spray-dried fish oil emulsions, J. Microencapsul., 20 (5):675-688 (2003).
Holub, Clinical nutrition: 4. Omega-3 fatty acids in cardiovascular care, Can. Med. Assoc. J., 166(5):608-615 (2002).

(Continued)

*Primary Examiner* — Helen F Heggestad
(74) *Attorney, Agent, or Firm* — Meunier Carlin & Curfman, LLC

(57) ABSTRACT

Disclosed are comestible emulsions that comprise polyunsaturated fatty acids and methods of preparing them. The emulsions remain clear or semi-clear upon dilution. The emulsions comprise one or more polyunsaturated fatty acids or derivatives thereof, one or more emulsifiers, one or more organic solvents, and one or more polyols in a water solution. The emulsions are particularly suited for incorporation into beverages.

52 Claims, No Drawings

(56) References Cited

OTHER PUBLICATIONS

Johnson et al., Chemical Processing and Micromixing in Confined Impinging Jets, AIChE J., 49(9):2264-2282 (2003).

Let et al., Protection against oxidation of fish-oil-enriched milk emulsions through addition of rapeseed oil or antioxidants, J. Agric. Food Chem., 53(13):5429-5437 (2005).

Little, Correlation of surfactant hydrophile-lipophile balance (HLB) with solubility parameter, Journal of Colloid and Interface Science, 65(3):587-588 (1978).

O'Keefe et al., Omega-3 Fatty Acids: Time for Clinical Implementation? Am J Cardiology, 85:1239-1241 (2000).

Omegavin package insert from Fresenius Kabi, Promedico Ltd, 4 Baltimore St. Petach-Tikva, Fresenius Kapi Austria Gmblt for Kabi Germany, pp. 1 and 2.

Panagiotou et al., Production of Polymer Nanosuspensions Using Microfluidizer® Processor Based Technologies, NSTI-Nanotech, 7(1):688-691 (2008).

Radack et al., The effects of low doses of n-3 fatty acid supplementation on blood pressure in hypertensive subjects: a randomized controlled trial, Arch. Intern. Med., 151:1173-1180 (1991).

Sugano, Balanced intake of polyunsaturated fatty acids for health benefits, J. Oleo Sci., 50(5):305-311 (2001).

Tang, Invention description of clear fish oil in water emulsion (Feb. 4, 2009).

Webb, Alternative sources of omega-3 fatty acids, Natural Foods Merchandiser, XXVI (8):40-44 (2005).

\* cited by examiner

COMESTIBLE EMULSIONS

CROSS REFERENCE TO RELATED APPLICATIONS

This application claims the benefit of priority to U.S. Provisional Application No. 61/380,577, filed Sep. 7, 2010, which is incorporated by reference herein in its entirety.

BACKGROUND

Polyunsaturated fatty acids (PUFAs), including omega-3, omega-6 and omega-9 fatty acids, are vital to everyday life and function. For example, the beneficial effects of omega-3 fatty acids like all-cis-5,8,11,14,17-eicosapentaenoic acid (EPA) and all-cis-4,7,10,13,16,19-docosahexaenoic acid (DHA) on lowering serum triglycerides are well established. All-cis-9,12,15-octadecatrienoic acid (ALA) is the precursor essential fatty acid of EPA and DHA. All-cis-5,8,11,14-eicosatetraenoic acid (AA) and its precursors all-cis-6,9,12-octadecatrienoic acid (GLA) and all-cis-9,12-octadecadienoic acid (LA) have been shown to be beneficial to infants.

Various of these compounds are also known for other cardioprotective benefits such as preventing cardiac arrhythmias, stabilizing atherosclerotic plaques, reducing platelet aggregation, and reducing blood pressure. See e.g., Dyrberg et al., In: Omega-3 Fatty Acids: Prevention and Treatment of Vascular Disease. Kristensen et al., eds., Bi & Gi Publ., Verona-Springer-Verlag, London, pp. 217-26, 1995; O'Keefe and Harris, *Am J Cardiology* 2000, 85:1239-41; Radack et al., "The effects of low doses of omega-3 fatty acid supplementation on blood pressure in hypertensive subjects: a randomized controlled trial." *Arch Intern Med* 151:1173-80, 1991; Harris, "Extending the cardiovascular benefits of omega-3 fatty acids." *Curr Atheroscler Rep* 7:375-80, 2005; Holub, "Clinical nutrition: 4 omega-3 fatty acids in cardiovascular care," *CMAJ* 166(5):608-15, 2002. Indeed, the American Heart Association has also reported that omega-3 fatty acids can reduce cardiovascular and heart disease risk. Other benefits of PUFAs are those related to the prevention and/or treatment of inflammation and neurodegenerative diseases, and to improved cognitive development. See e.g., Sugano and Michihiro, "Balanced intake of polyunsaturated fatty acids for health benefits." *J Oleo Sci* 50(5):305-11, 2001.

In addition to fish oil sources, PUFAs can be and are derived from microbial sources including, without limitation, *Mortiarella alpina* for ARA and various species of Thraustochytrids for DHA and EPA. Plants are now being modified genetically to include genes that produce various PUFAs in further efforts to reduce costs associated with commercial production of these oils.

Despite the strong evidence for the benefit of PUFAs in prevention of cardiovascular disease, the average daily consumption of these fatty acids by North Americans is estimated to be between 0.1 to 0.2 grams, compared to a suggested daily intake of 0.65 grams to confer benefit (Webb, "Alternative sources of omega-3 fatty acids." Natural Foods Merchandiser 2005, XXVI (8):40-4). Since altering dietary patterns of populations is difficult the supplementation of diets with PUFAs is an important approach to addressing this problem. Unfortunately, many PUFAs are sensitive to oxidation and can have unpleasant organoleptic properties. Further, compliance with dietary supplement regimens requires discipline, which is often wanting. In light of the health benefits of PUFAs it is desirable to find new ways to deliver these and other beneficial materials to a subject.

Delivery of PUFAs by formulating them into comestible compositions would be a desirable method from a consumer acceptability and compliance standpoint. However, the hydrophobicity and oxidative stability characteristics associated with many PUFAs creates significant challenges for incorporating them into comestible compositions. One approach involves the use of emulsions. Emulsions have been used as delivery vehicle for various substances. For example, emulsions have been used in the cosmetic, detergent, personal care, agricultural, and oil exploring industry. However, most emulsions are not water dilutable; that is, the emulsion becomes cloudy or milky white upon dilution by water. As such, there has been a good deal of interest in obtaining an emulsion that remains clear upon dilution and is stable over a long period of time. For commercial purposes, the creation of emulsions that remain clear upon dilution and are stable over a long period of time has been a goal. It is also of importance that the emulsion has a high loading factor, for more efficient delivery, and is inexpensive enough to be cost effective in cost sensitive beverages. The process for preparing such an emulsion must also be commercially cost effective. An emulsion with these properties can be incorporated in to waters and other clear or near clears beverages without affecting the beverage's underlying appearance and without significantly increasing the cost of the beverage to the consumer. This goal has not yet been satisfactorily attained with PUFAs, esters, and glycerides thereof.

U.S. Pat. No. 5,798,333 discloses a method of making a water dilutable, clear cyclosporine-in-water emulsion using tocophersolan (Vitamin E TPGS) as the emulsifier. This patent discloses the use of excess (7.5 times) emulsifier to dissolve cyclosporine. Cyclosporine has a low molecular weight and better solubility than various long chain PUFAs. The finished product is a semi-solid non-flowing gel contained in two-piece gelatine capsule.

International publication WO2009/117152 discloses a water dilutable, clear non-polar nanoemulsion containing Vitamin E TPGS, omega-3 triacylglycerol fish oil, and water. The ratio of emulsifier to fish oil is from 1.6:1 (w/w) to 6:1 (w/w). Also, additional components including benzyl alcohol, propylene glycol, glycerol, phospholipids, and a gum based emulsion stabilizers are used.

In another example, from U.S. Pat. No. 5,753,241, a very high pressure homogenization step at $10^8$ Pa was used to make the emulsion. However, such pressure is generally beyond the normal pressure range used in food applications, which is normally from 1500 psi to 6000 psi.

In light of the above, what are needed in the art are emulsions of PUFAs and other beneficial materials and methods for their preparation where the emulsion is not discernable in the liquid in which it is incorporated, has a high loading factor, has favourable organoleptic properties, and is cost effective. The compositions and methods disclosed herein meet these and other needs.

SUMMARY

In accordance with the purposes of the disclosed materials, compounds, compositions, articles, and methods, as embodied and broadly described herein, the disclosed subject matter, in one aspect, relates to compositions and methods for preparing and using such compositions. In a further aspect, the disclosed subject matter relates to emulsions. Also disclosed are methods of making and using the disclosed emulsions.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an emulsifier" includes mixtures of two or more such emulsifiers, reference to "the cosolvent" includes mixtures of two or more such cosolvents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data is provided in a number of different formats and that this data represents endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular component in a composition denotes the weight relationship between the component and any other components in the composition for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

"Subject," as used herein, means an animal. In one aspect, the subject is a mammal such as a primate, and, in another aspect, the subject is a human. The term "subject" also includes domesticated animals (e.g., cats, dogs, etc.), and livestock (e.g., cattle, horses, pigs, sheep, goats, etc.).

By "oil" is meant a composition containing one or more PUFAs, e.g., omega-3 fatty acids, omega-6 fatty acids, and/or omega-9 fatty acids, or derivatives thereof as described elsewhere herein. PUFAs can be in their free acid form, salt form, triacylglycerol ester form, phytosterol ester, and/or methyl or ethyl ester form and the term "oil" can include any one or more of these forms. Unless specifically stated, the term "oil" is used generally herein and is not meant to imply any specific level of purity, any specific level of hydrophobicity, any specific physical form or property, or any specific source. "Oil" unless stated otherwise, includes compositions derived from marine animal sources, e.g., fish, microbial sources, and/or plant sources. The term "oil" can be used synonymously with the term "dispersed phase" herein.

"Emulsion" is used herein to mean any heterogenous system that contains a disperse phase and continuous phase. The term is not intended to be limited by the particular size of the dispersed phase droplets or particles. The term "emulsion" used herein includes microemulsions and nanoemulsions.

A microemulsion is a thermodynamically stable emulsion that forms spontaneously.

A nanoemulsion is used to refer to a specific type of emulsion where the size of the particles or droplets in the dispersed phase is typically less than 0.1 µm.

"Clear" is used herein to refer to a characteristic of the disclosed emulsions. The clarity of an emulsion can be measured by various methods. However, unless stated otherwise, an emulsion that has an absorbance of less than about 0.1 A of a 1.3 cm thick sample at 400 nm is considered clear. A semi clear emulsion has an absorbance of from 0.3 A to about 0.1 A when measured at 400 nm in a 1.3 cm sample. By "dilutable clear emulsion" is meant that after dilution by water in any ratio, including diluting by water indefinitely, the emulsion's light absorbance does not become higher than about 1% of its value prior to dilution.

Reference will now be made in detail to specific aspects of the disclosed materials, compounds, compositions, articles, and methods, examples of which are illustrated in the accompanying Examples.

Materials and Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and a number of modifications that can be made to a number of components or residues of the compound are discussed, each and every combination and permutation that are possible are specifically contemplated unless specifically indicated to the contrary. Thus, if a class of components A, B, and C are disclosed as well as a class of components D, E, and F and an example of a combination composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Emulsions

Disclosed herein are emulsions that comprise a dispersed phase (e.g., oil) and a continuous phase. The dispersed phase can comprise one or more PUFAs and/or derivatives thereof. Also, present in the disclosed emulsions is one or more emulsifier, one or more co-solvent, and one or more mono and/or disaccharides.

In the disclosed emulsions, the ratio of emulsifier to dispersed phase is calculated by dividing the weight percent of the emulsifier in the emulsion by the weight percent of the dispersed phase. The disclosed emulsions have a ratio of emulsifier to dispersed phase of about 1.5 or less. That is, the amount of emulsifier used in the disclosed emulsions is slightly above, but in most cases approximately equal to or less than the amount of the dispersed phase. In some specific examples, the ratio of emulsifier to the dispersed phase is about 1.5, 1.4, 1.3, 1.2, 1.1, 1.0, 0.9, 0.8, 0.7, 0.6, or 0.5, where any of the stated values can form an upper or lower endpoint of a range, for example, from about 1.5 to about 0.1, from about 1.2 to about 0.3, from about 1 to about 0.5, or from about 1 to about 0.7.

Size

The disclosed emulsions can have droplets or particles of various sizes. For example, the disclosed emulsion can be up to about 200 nm, in particular less than about 100 nm. Specific examples include, but are not limited to, emulsions that have an average droplet size of less than about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 nm, where any of the stated values can form an upper or lower endpoint.

The size of the droplets can be determined by methods known in the art, such as light scattering, microscopy, spectroscopically, and the like.

Clarity

There are various methods by which the clarity of an emulsion can be measured or characterized. In some instances a turbidimeter can be used. Another method, which is used herein, is the spectroscopic measurement of absorbance. Specifically, the clarity of the disclosed emulsions is determined by diluting the emulsion with deionised water to have 50 mg of dispersed phase per 250 g of continuous phase. An ultrospectrometer, Ultrospec 2000 from Pharmacia Biotech (Cambridge, UK), is used to measure the light absorbance of the diluted emulsion sample at 400 nm. Pure deionised water is used as the reference. The dimension of the cuvettes is 4.5 cm by 1.3 cm by 1.3 cm. The clear emulsions disclosed herein have an absorbance at 400 nm of less than about 0.3, 0.2, or 0.1 A.

Dispersed Phase

The dispersed phase of the disclosed emulsions can comprise one, two, or even more components. For example, the dispersed phase can comprise one or more PUFAs and/or derivatives thereof. Derivatives of PUFAs can include alkyl esters (e.g., ethyl esters), glyceride esters (e.g., mono, di, and triacylglycerol), sterol esters (e.g., phytosterol esters), and salts of PUFAs. Mixtures and combinations of PUFAs and derivatives thereof are also suitable for use in the dispersed phases herein.

Specific examples of PUFAs include, but are not limited to, natural and synthetic, α-linolenic acid (18:3ω3)(ALA), octadecatetraenoic acid (18:4ω3)(Stearidonic acid), eicosapentaenoic acid (20:5ω3) (EPA), docosahexaenoic acid (22:6ω3) (DHA), docosapentaenoic acid (22:5ω) (DPA), eicosatetraenoic acid (24:4ω3), 16:3ω3, 24:5ω3, and/or nisinic acid (24:6ω3), arachidonic acid (20:4ω6)(ARA); others are noted elsewhere in the specification. These and other PUFAs, in either their free, esterified, or salt forms, can be found in and obtained from marine oils (e.g., fish oil, seal oil, krill oil), microbial oils (including natural as well as modified microbes whether by way of classical mutagenesis or genetic alteration) such as algae oil (e.g., microalgae oil), fungal oil, perilla oil, as well as plant oil (whether derived from naturally occurring plants or genetically modified plants), among others. Precursors of PUFAs, for example, ALA and GLA and derivatives such as polyglycolized derivatives or polyoxyethylene derivatives can also be present in the dispersed phase. In other specific examples, the dispersed phase can comprise DHA and/or EPA, a $C_1$-$C_6$ alkyl ester thereof, a triacylglycerol ester thereof, a phytosterol ester thereof, a salt thereof, and/or a mixture thereof.

In specific examples, the dispersed phase can comprise a microbial oil, for example, and algal oil (e.g., oil from a dinoflagellate such as *Crypthecodinium cohnii*) or fungal oil (e.g., oil from *Mortiarella Alpina, Thraustochytrium, Schizochytrium*, or a mixture thereof), and/or plant oil, including mixtures thereof.

In specific examples, the dispersed phase can comprise a marine oil, such as natural and refined and concentrated fish oil. Examples of suitable fish oils include, but are not limited to, Atlantic fish oil, Pacific fish oil, Mediterranean fish oil, light pressed fish oil, alkaline treated fish oil, heat treated fish oil, light and heavy brown fish oil, bonito oil, pilchard oil, tilapia oil, tuna oil, sea bass oil, halibut oil, spearfish oil, barracuda oil, cod oil, menhaden oil, sardine oil, anchovy oil, capelin oil, Atlantic cod oil, Atlantic herring oil, Atlantic mackerel oil, Atlantic menhaden oil, salmonid oil, tuna oil, and shark oil, including mixtures and combinations thereof. Non-alkaline treated fish oil is also a suitable loading substance. Other marine oils suitable for use herein include, but are not limited to, squid oil, octopus oil, krill oil, seal oil, whale oil, and the like, including mixtures and combinations thereof. Any PUFA oil and combination of PUFA oils can be used in the disclosed compositions and in the disclosed methods to prepare them.

The PUFAs disclosed herein can also be crude oils, semi-refined (also called alkali-refined), or refined oils from such sources disclosed herein. Still further, the disclosed emulsions can use oils comprising re-esterified triacylglycerols.

Further, the dispersed phase can be present in an amount of from about 1% to about 15% by weight of the emulsion. In specific examples, the dispersed phase can be present in an amount of from about 1% to about 15%, from about 3% to about 12%, from about 5% to about 10%, from about 7% to about 10%, or from about 8% to about 9% based on the total weight of the emulsion. In a preferred aspect, the dispersed phase is about 8.5% by weight of the emulsion.

Emulsifiers

The disclosed emulsions comprise one or more emulsifiers. In addition to being present with the dispersed phase in a particular ratio, the emulsifiers that are suitable for use herein have a HLB value of from about 10 to about 40. Typically, the emulsifier has an HLB value of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, where any of the stated values can form an upper or lower endpoint of a range. In specific examples, the emulsifier has an HLB of from about 12 to about 16, more specifically about 12 to 14, or about 13. HLB values can be calculated by Griffin's method (Griffin, W. C., Journal of the Society of Cosmetic Chemists 1, 311 (1949)) or other empirical method like solubility method (Little R. C., Journal of Colloid and Interface Science, 65(3): 587, 1978).

Vitamin E Derivatives

In various examples herein, the emulsifier is a polyalkylene glycol-derivative of Vitamin E, such as tocopherol and tocotrienol-derived emulsifiers in which the Vitamin E moiety represents the hydrophobic region of the emulsifier and is attached via a linker to a polyalkylene glycol. These emulsifiers can be formed via esterification of a tocopherol ester with a polyalkylene glycol. The tocopherol ester is made by esterification of tocopherol with the linker. The term tocopherol refers to any naturally occurring or synthetic form of vitamin E, and can refer to a single compound or a mixture. Examples of tocopherols include, for example, α-tocopherol, D-α-tocopherol, β-tocopherol, γ-tocopherol, and δ-tocopherol. The linker is a dicarboxylic acid (a carboxylic acid having two carboxy groups, e.g., succinic acid), such as succinic acid. Exemplary of dicarboxylic acids that can be used as linkers in these tocopherol and tocotrienol PEG diester emulsifiers are succinic acid, sebacic acid, dodecanedioic acid, suberic acid, or azelaic acid, citraconic acid, methylcitraconic acid, itaconic acid, maleic acid, glutaric acid, glutaconic acid, fumaric acids, and phthalic acids.

Suitable examples of Vitamin-E derived emulsifiers include, but are not limited to, polyethylene glycol (PEG) derivatives of tocopherol, such as tocopherol polyethylene glycol diesters (TPGD). A preferred emulsifier is tocopherol polyethylene glycol succinate (TPGS). TPGS analogs, TPGS homologs, and TPGS derivatives are also suitable. Other examples of emulsifiers include tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methyl citraconate polyethylene glycol, tocopherol itaconate polyethylene glycol, tocopherol maleate polyethylene glycol, tocopherol glutarate polyethylene glycol, tocopherol glutaconate polyethylene glycol, and tocopherol phthalate polyethylene glycol, among others.

Suitable emulsifiers can also include other PEG derivatives having similar properties, for example, PEG derivatives of sterols, e.g., a cholesterol or a sitosterol, and PEG-derivatives of other fat-soluble vitamins, for example, some forms of Vitamin A (e.g., Retinol) or Vitamin D (e.g., Vitamin D1-D5).

In a preferred aspect, the emulsifier comprises tocopherol polyethylene glycol succinate (TPGS), such as a TPGS-1000 and/or a d-α TPGS. In another example, the emulsifier is a TPGS analog. TPGS analog refer to compounds, other than TPGS, that are similar to a parent TPGS compound, but differ slightly in composition, for example, by the variation, addition or removal of an atom, one or more units (e.g., methylene unit(s)-$(CH_2)_n$) or one or more functional groups. TPGS analogs include Vitamin E derived surfactants, including PEG derivatives of Vitamin E, including vitamin E PEG diesters, such as, but not limited to, tocopherol polyethylene glycol sebacate (PTS), tocopherol polyethylene glycol dodecanodioate (PTD), tocopherol polyethylene glycol suberate (PTSr), tocopherol polyethylene glycol azelaate (PTAz), and polyoxyethanyl tocotrienyl sebacate (PTrienS) as well as other PEG derivatives of Vitamin E.

The PEG moieties in the PEG-derived emulsifier, including the PEG moieties in the PEG-derivatives of Vitamin E, include PEG moieties selected from among any one or more of PEG-OH, PEG-NHS, PEG-CHO, PEG-SH, PEG-NH$_2$, PEG-CO$_2$H, methylated PEGs (m-PEGs) and branched PEGs, and includes PEG moieties having a molecular weight of from about 200 kDa to about 20,000 kDa, from about 200 kDa to about 6,000 kDa, from about 600 kDa to about 6,000 kDa, from about 200 kDa to about 2,000 kDa, from about 600 kDa to about 1,500 kDa, or from about 600 kDa to about 1,000 kDa.

Preferred examples of suitable emulsifiers are vitamin E polyethylene glycol (PEG)-derived emulsifiers, such as tocopherol polyethylene glycol succinate (TPGS) with a HLB of from about 12 to about 14 (e.g., about 13).

Desirably, the emulsifiers are acceptable by food regulatory authorities at their particular level of use. For example, TPGS-1000, which has a PEG moiety of 1000 kDa, is considered food grade and is sold under the name Eastman Vitamin E TPGS™, by Eastman Chemical Company, Kingsport, Tenn., USA. This TPGS is a water-soluble form of natural-source Vitamin E, which is prepared by esterifying the carboxyl group of crystalline d-alpha-tocopheryl acid succinate with polyethylene glycol 1000 (PEG 1000), and contains between 260 and 300 mg/g total tocopherol. A similar compound can be made by esterifying the carboxyl group of the d,l form of synthetic Vitamin E with PEG 1000. This tocopheryl polyethylene glycol is a water-soluble preparation of a fat-soluble vitamin (Vitamin E), for example, as disclosed in U.S. Pat. Nos. 3,102,078, 2,680,749 and U.S. Published Application Nos. 2007/0184117 and 2007/0141203. Also exemplary of the TPGS surfactant that can be used in the provided compositions is the Water Soluble Natural Vitamin E (TPGS), sold by ZMC-USA, The Woodlands, Tex., USA.

Polysorbates

In other examples, the emulsifiers can be polysorbates. Polysorbates are oily liquids derived from PEG-ylated sorbitan (a derivative of sorbitol) esterified with fatty acids. Examples of suitable polysorbates are polysorbate 20 (Tween 20 or polyoxyethylene (20) sorbitan monolaurate), polysorbate 40 (Tween 40 or polyoxyethylene (20) sorbitan monopalmitate), polysorbate 60 (Tween 60 or polyoxyethylene (20) sorbitan monostearate), and polysorbate 80 (Tween 80 or polyoxyethylene (20) sorbitan monooleate). The number following the polyoxyethylene part refers to the total number of oxyethylene —$(CH_2CH_2O)$— groups found in the molecule. The number following the polysorbate part is related to the type of fatty acid associated with the polyoxyethylene sorbitan part of the molecule. Monolaurate is indicated by 20, monopalmitate is indicated by 40, monostearate by 60 and monooleate by 80.

In certain examples the emulsifier is not lecithin.

Solvents

The continuous phase of the disclosed emulsions comprises water. However, additional solvents (i.e., co-solvents) can also be present in the continuous phase and in some cases are preferred. For example, a polar solvent such as propylene glycol, glycerol, and glycerine can be used. These co-solvents can be present in an amount of from about 1% to about 45% by weight of the emulsion. In specific example, the co-solvent is present at from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, and 45% by weigh of the composition where any of the values can form an upper or lower endpoint of a range, for example, from about 5% to about 20%, from about 9% to about 18%, from about 13% to about 17%, from about 13% to about 17%, from about 14% to about 16%, from about 20% to about 45%, or about 15% by weight of the emulsion.

In the disclosed emulsions, the amount of water is from about 13 to about 25% by weight of the emulsion, for example, about 13, 14, 15, 16, 17, 18, 19, 20, 21, 22, 23, 24, and 25% by weight of the emulsion, where any of the stated values can form an upper or lower endpoint of a range, for example, from about 14% to about 22%, from about 17% to about 20%, from about 17% to about 25%, from about 20% to about 23%, from about 21% to about 24%, and from about 22% to about 25% by weight of the emulsion.

In general, the total amount of the solvent (both water and any co-solvent) is less than about 50% by weight of the total emulsion. In various examples, the total amount of solvent in the disclosed emulsions is less than about 45%. Still further, the total amount of solvent in the emulsion is about 30, 31, 32, 33, 34, 35, 36, 37, 38, 39, 40, 41, 42, 43, 44, 45, 46, 47, 48, 49, or 50% by weight of the emulsion, where any of the stated values can form the upper or lower endpoint of a range, for example from about 30% to about 50%, from about 32% to about 45%, from about 34% to about 42%, from about 36% to about 40%, or from about 37 to about 38% by weight of the emulsion.

In certain examples the emulsion are substantially free of benzyl alcohol, for example, less than about 5, 4, 3, 2, or 1% of benzyl alcohol, or about 0% benzyl alcohol by weight of the emulsion.

Mono and Disaccharides

The continuous phase of the disclosed emulsions also comprises one or more mono- and/or di-saccharides. Examples of monosaccharides include glucose, fructose, galactose, arabinose, ribose, ribulose, xylose, mannose, and xylulose. Examples of di-saccharides include sucrose, lactose, cellobiose, sorbose, trehalose, maltose, and raffinose and the like. Various saccharide derivatives such as xylitol, sorbitol, and isomalt are also suitable for use in the disclosed emulsions.

In general, the total amount of the mono- and or di-saccharide is greater than about 40% by weight of the total emulsion. In various examples, the total amount of these sugars in the disclosed emulsions is from about 30% to about 66% by weight of the emulsion. Still further, the total amount of solvent in the emulsion can be about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, and 66% by weight of the emulsion, where any of the stated values can form the upper or lower endpoint of a range, for example from about 40 to about 66%, from about 45% to about 50%, from about 46% to about 48%, from about 48% to about 50%, from about 47% to about 49%, or from about 45 to about 47% by weight of the emulsion.

The disclosed compositions are also substantially free of polysaccharides, such as gums, for example, less than about 5, 4, 3, 2, or 1% of polysaccharide, or about 0% polysaccharide by weight of the emulsion. The disclosed emulsions can, in some instances, be substantially free of fructose corn syrup.

Antioxidants

The emulsions disclosed herein can also contain an antioxidant. The antioxidant can be present in the continuous phase and/or the dispersed phase. Suitable examples of antioxidants include, but are not limited to, a phenolic compound, a plant extract, or a sulphur-containing compound. In certain examples disclosed herein the antioxidant can be ascorbic acid or a salt thereof, e.g., sodium ascorbate. In other examples, the antioxidant can be vitamin E, CoQ10, tocopherols, lipid soluble derivatives of more polar antioxidants such as ascobyl fatty acid esters (e.g., ascobyl palmitate), plant extracts (e.g., rosemary, sage and oregano oils, green tea extract), algal extracts, and synthetic antioxidants (e.g., BHT, TBHQ, ethoxyquin, alkyl gallates, hydroquinones, tocotrienols).

Method of Preparing Emulsions

Methods for preparing the disclosed emulsions are also described herein. In general, the disclosed emulsions can be prepared by emulsifying a mixture of the emulsifier, the dispersed phase (e.g., the oil), the solvent, and the mono- and/or di-saccharide. As a more specific example, the emulsifier is first melted if necessary and then mixed with the components of the dispersed phase and co-solvent(s). The ratio of emulsifier to dispersed phase is about 1.5 or less. The concentration of the emulsifier in this first mixture is above the emulsifiers' Critical Micelle Concentration (CMC), so nano-scaled emulsifier micelles containing the dispersed phase are formed. The co-solvent also helps the emulsifier micelles disperse and avoid gelation of some of the emulsifiers when they are in contact with water.

The mixture can then be combined with a solution of mono- and/or di-saccharide in water. While not wishing to be bound by theory, this sugar solution has two functions: first, the sugar solution increases viscosity and facilitates the particle size reduction by homogenization in the next step; second, the sugar acts as a stabilizer for the emulsion and avoids the formation of liquid crystals which causes the aggregation of droplets and cloudiness for the emulsion.

The final mixture can then be homogenized. The homogenization is used to reduce the droplets size of the emulsion. Because small amounts of emulsifier are used in the first step and the emulsifier concentration is diluted in the second step, the emulsion that comes out of the second step is not a microemulsion and the droplets size is above 100 nm. To reduce the emulsion droplet size, for example, to less than 100 nm, and to have a clear emulsion a high-pressure homogenization can be used. The number of passes that may be needed is dependent on the pressure applied. For 5000 psi, five to ten passes will usually be sufficient. Typical pressures that can be uses are from about 1500 to about 6000 psi. Microfluidizer processor based technologies can also be used to prepare the emulsions.

The emulsification step can be performed at a suitable temperature given the melting point of the oil and to reduce chances of oxidation. For example, emulsification can be from about −4 to about 80° C., from about 0 to about 20° C., from about 30° C. to about 60° C., or from about 40° C. to about 50° C.

Antioxidants as noted herein can be added in either the continuous or dispersed phase to protect the oils. These can be added at any step during the emulsion formation process. What step the antioxidant is added, and at what amount, will depend on the particular antioxidant.

Methods of Use

The disclosed emulsions can be used to prepare comestible compositions in order to deliver oils to a subject. In a particular example, the disclosed emulsions can be added to a beverage so that the beverage can become a source of PUFAs and derivatives thereof. In another particular example, disclosed herein are methods of supplementing PUFAs and derivatives thereof in a subject by administering an effective amount of an emulsion disclosed herein. In another example, disclosed herein are methods of treating various human conditions including, but not limited to, lowering cholesterol levels, triglyceride levels, or combinations thereof in a subject by administering an effective amount of an emulsion disclosed herein.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, pH, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, temperatures, pressures, and other reaction ranges and conditions that can be used to optimize the product purity and yield obtained from the described process. Only reasonable and routine experimentation will be required to optimize such process conditions.

Certain materials, compounds, compositions, and components disclosed herein can be obtained commercially or readily synthesized using techniques generally known to those of skill in the art. For example, the starting materials and reagents used in preparing the disclosed compositions are either available from commercial suppliers such as Ocean Nutrition Canada Limited (Dartmouth, Canada), Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Examples 1-7

Vitamin E TPGS-Based Clear Micro- and Nanoemulsions

Various examples were prepared using the ingredients in the amounts noted in Table 1. Vitamin E TPGS (Zhejiang Medicine Company, Xinchang, Zhejiang, China) was melted using a water bath set at 60° C. The melted TPGS, propylene glycol, glycerol (Nealander International Inc., Mississauga, Canada) and fish oil (Ocean Nutrition Canada Limited, Dartmouth, Canada) were then mixed together. Certain examples (as noted in Table 2) were added slowly into a 66.7% aqueous sugar solution. The resulting mixture was then added to DI water with mixing until a clear emulsion formed. Homogenization at 5000 psi was then performed for 10 passes. Droplet size of the emulsions was about 72 nm as determined by Particle Analyzer Beckman Coulter LS230. The emulsions remained clear after dilution by water in any ratio. Storage was at 4° C.

The clarity of most of the emulsion samples was tested by light absorbance of a 0.94% solution in DI water (0.94 g emulsion/100 g water to give 50 mg of EPA+DHA per 250 g of serving) at 400 nm-0.068 (DI water as a reference).

TABLE 1

Formula of emulsions made with Vitamin E TPGS emulsifier, different oils, and different emulsifier/oil ratio.

| Ingredients (in wt. %) | Example No. | | | | | | |
| --- | --- | --- | --- | --- | --- | --- | --- |
| | Comp 1 | Comp 2 | 3 | 4 | 5 | 6 | 7 |
| Vitamin E TPGS* | 19.3 | 19.9 | 8.5 | 5.4 | 6.0 | 6.8 | 5.4 |
| Lecithin | — | — | — | — | — | — | 1.3 |
| Propylene glycol | 4.1 | 4.8 | 8.5 | 5.3 | 6.0 | 6.8 | 5.3 |
| Glycerol | 1.9 | 1.9 | 7.9 | 8.0 | 6.0 | 6.8 | 8.0 |
| Sugar | — | — | 44.4 | 48.3 | 49.0 | 47.3 | 47.4 |
| Water | 65.7 | 64.9 | 22.2 | 24.2 | 24.5 | 23.7 | 23.7 |

TABLE 1-continued

Formula of emulsions made with Vitamin E TPGS emulsifier, different oils, and different emulsifier/oil ratio.

| Ingredients | Example No. | | | | | | |
|---|---|---|---|---|---|---|---|
| (in wt. %) | Comp 1 | Comp 2 | 3 | 4 | 5 | 6 | 7 |
| Omega-3 Oil | $8.9^A$ | $8.5^B$ | $8.5^B$ | $8.8^C$ | $8.5^C$ | $8.5^C$ | $8.8^C$ |
| HLB | 13.2 | 13.2 | 13.2 | 13.2 | 13.2 | 13.2 | 12 |
| Emulsifier/Oil ratio | 2.1 | 2.3 | 1.0 | 0.61 | 0.7 | 0.8 | 0.72 |
| Light absorbance at 400 nm (A) | — | — | 0.068 | 0.117 | 0.105 | 0.098 | 0.073 |

$^A$30TG Omega-3 Fish Oil (270 mg/g EPA + DHA; 320 mg/g total Ω-3 in TG form)
$^B$30TG Omega-3 Fish Oil (290 mg/g EPA + DHA; 350 mg/g total Ω-3 in TG form)
$^C$30TG Omega-3 Fish Oil (250 mg/g EPA + DHA; 300 mg/g total Ω-3 in TG form)

Examples 1 and 2 are comparative examples in that the ratio of emulsifier to dispersed phase (in these cases omega-3 fish oil) is 2.1 and 2.3. No sugar was used in Examples 1 and 2 either and the amount of co-solvent was relatively low.

Examples 8-12

Micro- and Nanoemulsions Using Various Emulsifiers

The method described for Examples 1-7 above was followed using various other emulsifiers. Examples 8-12 used emulsifiers that have similar or different HLB values. The various examples were prepared using the ingredients in the amounts noted in Table 2.

The oil was combined with polysorbate, propylene glycol, soy lecithin (Solae Company, St. Louis, Mo., U.S.), sodium dodecyl sulphate, and or monoglyceride (Abitech, Northampton, UK) as noted on Table 2 to form a homogeneous mixture. The mixture was then slowly added in to a 66.7% sugar solution under mixing. Glycerol was added as noted in Table 2. The mixture was stirred for 5 minutes and then homogenized at 5000 psi using a microfluidizer for 10 passes. Storage was at 4° C.

The clarity of most of the emulsion samples was tested by light absorbance of a 1.8% solution in DI water (1.8 g emulsion/100 g water to give 50 mg of EPA+DHA per 250 g of serving) at 400 nm-0.052 (DI water as a reference).

TABLE 2

Formula of emulsions with different HLB values made with different emulsifiers and different oils.

| Ingredients | Example No. | | | | |
|---|---|---|---|---|---|
| (in wt. %) | 8 | 9 | 10 | 11 | Comp 12 |
| Polysorbate 80 | — | — | — | — | 7.7 |
| Polysorbate 85 | 6.6 | 6.6 | — | — | — |
| Sodium dodecyl sulfate | — | — | 0.9 | 0.8 | — |
| Propylene glycol | 4.4 | 4.4 | 8.8 | 8.3 | 4.4 |
| Glycerol | 4.0 | 4.0 | — | — | 4.0 |
| Lecithin | 2.2 | 2.2 | — | — | — |
| Monoglyceride | — | — | — | — | 1.2 |
| Sugar | 52.2 | 52.2 | 58.7 | 55.1 | 52.2 |
| Water | 26.1 | 29.4 | 29.4 | 27.5 | 26.2 |
| Omega-3 Oil | $4.5^A$ | $4.4^A$ | $2.2^B$ | $8.3^B$ | $4.4^A$ |
| HLB | 10 | 10 | 40 | 40 | 13.5 |
| Emulsifier/Oil ratio | 1.5 | 1.5 | 0.4 | 0.1 | 1.8 |
| Light absorbance at 400 nm (A) | — | 0.052 | 0.018 | 0.046 | 0.012 |

$^A$Winterized 30TG Omega-3 Fish Oil (546 mg/g EPA + DHA in TG form)
$^B$30TG Omega-3 Fish Oil (250 mg/g EPA + DHA; 300 mg/g total Ω-3 in TG form)

These examples indicate that the disclosed methods are relatively independent of an emulsifier's HLB value. Thus, a wide range of emulsifiers with various HLB values can be used.

Organoleptic Evaluations of Clear Omega-3 Oil-in-Water Emulsions in Beverages

The emulsion in Comparative Example 2 was tested in several beverages. All beverages were pasteurized. The emulsion was added before pasteurization at a dosage level of 32 mg of EPA+DHA per 500 gram of serving. "Flavour Acceptability" was scaled from 1 to 7, with 1 being the most acceptable and 7 being the most unacceptable. Four to five panelists participated in the sensory evaluation. Any sample with a "Flavour Acceptability" score greater than 4 was rejected. Results are shown in Table 3.

TABLE 3

Organoleptic results of beverages fortified with fish oil-in-water emulsion.

| Storage time | Flavour Acceptability After Storing Under 4° C. | | | | | | | |
|---|---|---|---|---|---|---|---|---|
| (Days) | 1 | 7 | 14 | 21 | 28 | 35 | 42 | 49 | 56 |
| Lemon-Lime GATORADE ™ | 1.5 | 2.2 | 3 | 3 | 2.75 | 2.5 | 2.125 | 2.5 | 4 |

TABLE 3-continued

Organoleptic results of beverages fortified with fish oil-in-water emulsion.

| Storage time | Flavour Acceptability After Storing Under 4° C. | | | | | | | | |
|---|---|---|---|---|---|---|---|---|---|
| (Days) | 1 | 7 | 14 | 21 | 28 | 35 | 42 | 49 | 56 |
| Apple Juice | 4 | 4.4 | 4.5 | 6 | | | discarded | | |
| Orange GATORADE ™ | 2 | 1.8 | 2 | 3 | 1.75 | 2.5 | 1.75 | 1.25 | 2.25 |
| Fruit Punch | 3.75 | 4.4 | 5.25 | 4.75 | | | discarded | | |

Vitamin E TPGS-based omega-3 oil-in-water clear emulsion can be used to fortify orange GATORADE™ at 32 mg of EPA+DHA per 500 grams of serving. The sensory of the fortified GATORADE™ is acceptable after storage of up to 56 days. Lemon-Lime GATORADE™ was acceptable up to 56 days.

To evaluate two clear emulsion formulas: 1:1 and 2:1 at various of PUFA level in Orange GATORADE™ including 20 mg, 32 mg, and 50 mg per 250 g of serving. The formula of clear emulsion sample 1:1 is the same as the formula shown in Example 3, and the formula of clear emulsion sample 2:1 is the same as the formula shown in Comparative Example 2. Flavour Acceptability was determined as noted above with a score below 4 being acceptable. Fishiness was based on a scale of from 0 to 6, with 0 being completely no fishy taste and 6 being totally fishy. A fishiness score below 2.0 is acceptable. Results are shown in Table 4.

TABLE 4

Organoleptic results of orange GATORADE ™ fortified with fish oil-in-water emulsion

| Emulsifier:oil ratio | Dosage of EPA + DHA/ 250 g | Flavour | Relative to control (0) | Acceptability (1-7) | Fishiness (0-6) |
|---|---|---|---|---|---|
| Control | — | — | 0 | 1.0 | 0.0 |
| 1:1 | 20 | oranges, perfumy, sweet, tart, slightly salty, | 0.3 | 1.9 | 0.1 |
| 1:1 | 32 | oranges, perfumy, sweet, muted, soapy, floral aftertaste, slightly off, muted | 0.4 | 1.6 | 0.1 |
| 1:1 | 50 | oranges, perfumy, sweet, slightly oily texture, slightly muted, fishy, tart, slightly soapy, slightly soapy | 0.6 | 2.2 | 0.4 |
| 2:1 | 20 | oranges, perfumy, sweet, green, tart, very slightly soapy, | 0.3 | 1.8 | 0.1 |
| 2:1 | 32 | oranges, perfumy, sweet, slightly plastic, slightly green, tart, floral, slightly soapy, fatty, slightly more sour | 0.6 | 2.1 | 0.0 |
| 2:1 | 50 | oranges, perfumy, sweet, slightly bitter, green, citrusy, floral, slightly soapy, green, fatty | 0.4 | 2.1 | 0.2 |

Vitamin E TPGS-based PUFA oil-in-water emulsion can be used to fortify Orange GATORADE™ at up to 50 mg of EPA+DHA per 250 grams of serving. The sensory of the fortified GATORADE™ is acceptable in the beginning of the test.

The organoleptic acceptability of Lemon-Lime GATORADE™ fortified by PUFAs oil-in-water emulsions was evaluated by preparing samples at a dosage level of 50 mg of EPA+DHA per 250 gram serving and with different antioxidants. The base formula of clear emulsion, before adding different antioxidants, used the same emulsifier:oil ratio as that of Example 3: specifically, Vitamin E TPGS (4.38%); 30TG Omega-3 fish oil (4.38%); propylene glycol (4.38%); sugar (55.8%); water (27.9%); and glycerol (3.2%) (total 100%).

Different antioxidants including citric acid, ascorbic acid, green tea extract from Taiyo International Inc. (Minneapolis, Minn.) and 20M green tea extract from Danisco Canada Inc. (Scarborough, Canada) were added separately to obtain the desired antioxidants concentration specified in Table 5.

An accelerated shelf-life study was used to estimate the shelf life of the fortified GATORADE™. All the samples were stored at 35° C. in dark and tasted biweekly. Results are shown in Table 5.

It is possible to use Vitamin E TPGS based fish oil-in-water emulsion to fortify Lemon-Lime GATORADE™ with PUFAs. The fortified beverage can have a shelf-life of 6-8 months.

TABLE 5

Organoleptic Evaluation of Lemon-Lime GATORADE ™ with 50 mg of
EPA + DHA through fish oil-in-water emulsion and with different antioxidants.

| Sample composition | Flavour acceptability | | | | | Fishiness | | | | |
|---|---|---|---|---|---|---|---|---|---|---|
| at 35° C. | Day 1 | Wk 2 | Wk 4 | Wk 6 | Wk 8 | Day 1 | Wk 2 | Wk 4 | Wk 6 | Wk 8 |
| 1:1, no antioxidants or AP[a] in water phase | 1.8 | 3.2 | — | — | — | 0.2 | 1.4 | — | — | — |
| 0.8% Citric acid, 4.09% fish oil | 1.3 | 3.4 | — | — | — | 0 | 1.4 | — | — | — |
| 0.5% Citric acid, 4.22% fish oil | 1.8 | 3.8 | — | — | — | 0.2 | 2 | — | — | — |
| 0.5% Citric acid, 33.33% HFCS[b] | 1.8 | 3.6 | — | — | — | 0.2 | 1.4 | — | — | — |
| 0.2% Citric acid | 1.6 | 3.4 | — | — | — | 0 | 1.6 | — | — | — |
| 2% Ascorbic acid, | 1.8 | 4 | — | — | — | 0.3 | 1.8 | — | — | — |
| 1% Ascorbic acid, 3.97% fish oil | 3.3 | 4.6 | — | — | — | 1 | 2.2 | — | — | — |
| 1% Ascorbic acid, 33.33% HFCS | 1.8 | 5 | — | — | — | 0 | 3.4 | — | — | — |
| 0.5% Ascorbic acid | 1.3 | 5.6 | — | — | — | 0 | 3 | — | — | — |
| 0.05% Danisco Green Tea extract 20M | 1.4 | 3.4 | — | — | — | 0 | 1 | — | — | — |
| 0.05% 20M, 33.33% HFCS | 1 | 3.6 | — | — | — | 0 | 0.8 | — | — | — |
| 0.1% Danisco Green Tea extract 20M | 1 | 2.4 | 3.3 | 3.6 | 5.2 | 0 | 0.4 | 1 | 1.5 | 3 |
| 0.05% Taiyo Green Tea extract, 4.35% Fish Oil | 1.5 | 3.3 | — | — | — | 0.2 | 1.4 | — | — | — |
| 0.1% Taiyo Green Tea extract, 4.35% Fish Oil | 2 | 3.3 | — | — | — | 0.4 | 1.2 | — | — | — |
| 0.1% Taiyo Green Tea extract, 33.33% HFCS | 1.4 | 3.6 | — | — | — | 0 | 1.8 | — | — | — |
| 0.2% Taiyo Green Tea extract, 4.13% Fish Oil | 1.8 | 2.4 | 3.2 | 3.6 | 4.7 | 0.4 | 0.8 | 1.2 | 1.8 | 3.2 |
| 551 ppm AP, 5.8% Fish Oil | 2.2 | 2.4 | 3.8 | — | — | 0.4 | 0.4 | 1.8 | — | — |

[a]AP—Ascorbyl palmate
[b]HFCS—High fructose corn syrup
It is noted that some fish oils already have antioxidants added to them. For example, fish oils can contain Duralox, which is a mixture of citric acid with mixed natural tocopherol and rosemary extract. Thus, the antioxidants listed in Table 6 are in addition to those already present in the oils.

Comparative Examples 13-23

Polysorbate-Based Clear Microemulsion

Various examples were prepared using the ingredients in the amounts noted in Table 6. Sugar (Redpath Sugar Ltd., Toronto, Canada) was dissolved in DI water to make a 50% sugar solution. Polysorbate 80 (Sigma-Aldrich, Co., St. Louis, Mo., USA), propylene glycol (Fisher Scientific Inc. Ottawa, Canada), polysorbate 85 (Sigma-Aldrich, Co., St. Louis, Mo., USA), and omega-3 oil (Ocean Nutrition Canada Limited, Dartmouth, Canada) were then added to the sugar solution. The mixture was then emulsified until it became clear by visual inspection. Storage was at 4° C.

All of the emulsions remained clear for more than a year by checking visually. They also remained clear when diluted by water in any ratio. The clearness was checked visually against water. Some were checked by spectroscopic methods as disclosed hereinabove. For example, the dilution of the emulsion from Example 16 in Table 2 at 0.9% concentration, which gives 50 mg of EPA+DHA per 250 g serving, had light absorbance of 0.024 A at 400 nm. Some sugar crystals crystallized out of the emulsion, but it did not affect the clearness of the emulsion and the dilution of the emulsion.

TABLE 6

Formula of emulsions made with polysorbate-based emulsifiers and different PUFAs.

| Ingredients | Example No. | | | | | | | | | | |
|---|---|---|---|---|---|---|---|---|---|---|---|
| (in wt. %) | 13 | 14 | 15 | 16 | 17 | 18 | 19 | 20 | 21 | 22 | 23 |
| Polysorbate 80 | 52.1 | 59.6 | 43.5 | 43.4 | 43.5 | 43.4 | 42.0 | 42.2 | 43.4 | 42.1 | 35.1 |
| Polysorbate 85 | — | 3.0 | 2.2 | 2.3 | 2.2 | 2.3 | 5.8 | 5.4 | 5.5 | 5.0 | 14.2 |
| Propylene glycol | 41.7 | 29.9 | 21.7 | 22.2 | 21.7 | 22.2 | 21.0 | 21.1 | 20.7 | 21.8 | 20.1 |

TABLE 6-continued

Formula of emulsions made with polysorbate-based emulsifiers and different PUFAs.

| Ingredients (in wt. %) | Example No. | | | | | | | | | | |
|---|---|---|---|---|---|---|---|---|---|---|---|
| | 13 | 14 | 15 | 16 | 17 | 18 | 19 | 20 | 21 | 22 | 23 |
| Abimono 90 LS | 2.9 | — | — | — | — | — | — | — | — | — | — |
| Sugar | — | — | 13.6 | 13.3 | 13.6 | 13.3 | 13.0 | 12.9 | 12.5 | 12.4 | 10.2 |
| Water | — | — | 13.6 | 13.3 | 13.6 | 13.3 | 13.0 | 12.9 | 12.5 | — | — |
| Omega-3 Oil | $3.2^C$ | $7.5^A$ | $5.4^A$ | $5.6^B$ | $5.4^A$ | $5.6^B$ | $5.3^D$ | $5.6^E$ | $5.3^F$ | $5.6^G$ | $10.3^G$ |
| HLB | 14.5 | 14.8 | 14.8 | 14.8 | 14.8 | 14.8 | 14.5 | 14.5 | 14.5 | 14.6 | 13.8 |
| Emulsifier/ Oil ratio | 17.2 | 8.3 | 8.5 | 8.2 | 8.5 | 8.2 | 9.1 | 8.5 | 9.2 | 8.4 | 4.8 |

$^A$Ethyl Ester Omega-3 Fish Oil (660 mg/g EPA + DHA; 740 mg/g total 51-3 in EE form)
$^B$Winterized Omega-3 Fish Oil (546 mg/g EPA + DHA in TG form)
$^C$30 TG Omega-3 Fish Oil (270 mg/g EPA + DHA; 320 mg/g total Ω-3 in TG form)
$^D$Winterized Omega-3 Algae Oil (350 mg/g EPA + DHA)
$^E$Winterized Omega-3 Fish Oil Marine 18/12 TG (250 mg/g EPA + DHA; >300 mg/g total Ω-3 in TG form)
$^F$Winterized Omega-3 Fish Oil Side stream EX EPA 27/15 (420 mg/g EPA + DHA)
$^G$Winterized Omega-3 Fish Oil XB 18/12 TG Winterized (287 mg/g EPA + DHA in TG form)

These examples reveal that clear emulsions with PUFAs can be prepared with polysorbate-based emulsifiers, but great excess of these particular emulsifiers to oil are used.

Comparative Example 24

The procedure set forth in Example 1 of U.S. Pat. No. 5,753,241 was followed except that the emulsifiers disclosed therein were replaced with Vitamin E TPGS (Zhejiang Medicine Company, Xinchang, Zhejiang, China), and ethanol was replaced by propylene glycol (Fisher Scientific Inc. Ottawa, Canada). The ingredients and amounts are shown in Table 7. Further the emulsion was homogenized at 5000 psi using Microfluidizer (Microfluidics, Newton, Mass., USA) for 15 passes to be comparable to Example 6 in Table 1 above where the emulsifier/oil ratio=0.8.

TABLE 7

| Ingredients | Weight (g) | Percentage (%) |
|---|---|---|
| Vitamin E TPGS | 20.4 | 6.8 |
| Fish Oil | 25.5 | 8.5 |
| Propylene glycol | 45 | 15 |
| Water | 191.4 | 63.8 |
| Glycerol | 17.7 | 5.9 |
| Total | 300 | 100 |

Light absorbance of dilution (0.94 g emulsion/100 g water to give 50 mg EPA+DHA per 250 g of water serving at 400 nm is 0.419, which is not clear or semi-clear. The corresponding sample in Table 1 (i.e., Example 6) has light absorbance of 0.098. Thus, the presence of sugar made a dramatic difference in clarity.

Comparative Example 25

The procedure set forth in Example 1 of U.S. Pat. No. 5,798,333 was followed except that cyclosporine was replaced by 30TG fish oil. The ingredients and amounts are shown in Table 8.

TABLE 8

| Ingredients | Weight (g) | Percentage (%) |
|---|---|---|
| Vitamin E TPGS | 8 | 28.6 |
| Fish Oil (30 TG) | 10 | 35.7 |
| Propylene glycol | 10 | 35.7 |
| Total | 28 | 100 |

Light absorbance of dilution (0.23 g emulsion/100 g water to give 50 mg EPA+DHA per 250 g of water serving) at 400 nm was 1.237, which is not clear or semi-clear. The corresponding sample in Table 1 (i.e., Example 6) has light absorbance of 0.098.

Comparative Example 26

The procedure set forth in WO 2009/117152, page 155 to 157, was followed using the formula in Table 2A (ix), but a reduced amount of Vitamin E TPGS was used to make it comparable to Example 6 in Table 1 herein, which has an emulsifier/oil ratio=0.8. The ingredients and amounts are shown in Table 9. Also, the sample was homogenized at 7400 rpm using Polytron PT 6100 for 10 min instead of 850 rpm to 1200 rpm using a CJ-4E reversible homogenizer (Arde Barinco, Inc.)

TABLE 9

| Ingredients | Phase | Weight (g) | Percentage (%) |
|---|---|---|---|
| Fish Oil (30 TG) | Oil | 40 | 10 |
| Water | Water | 325.2 | 81 |
| Saladizer (TIC Gum, White Marsh, MD) | Water | 0.8 | 0.2 |
| Vitamin E TPGS | Oil | 32 | 8 |
| Saladizer | Oil | 0.254 | 0.06 |
| Benzyl alcohol | Oil | 2.0 | 0.5 |
| Citric acid | Emulsion | 1.12 | 0.3 |
| Total | | 28 | 100 |

Light absorbance of dilution (0.8 g emulsion/100 g water to give 50 mg EPA+DHA per 250 g of water serving) at 400 nm is 2.162, which is not clear or semi-clear. The corresponding sample in Table 1, i.e., Example 6, has light absorbance of 0.098.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An emulsion, comprising:
   a. from about 4 to about 15 wt. % of a polyethylene glycol derivative of a fat-soluble vitamin emulsifier;
   b. from about 5 to about 10 wt. % of a dispersed phase, wherein the dispersed phase comprises one or more polyunsaturated fatty acids or derivatives thereof;
   c. from about 20 to about 25 wt. % of water;
   d. from about 5 to about 18 wt. % of a co-solvent; and
   e. from about 40 to about 55 wt. % of a mono-saccharide, a di-saccharide or both,
   wherein the ratio of the emulsifier to the dispersed phase is about 1.5 or less, and wherein the combined amount of water and co-solvent is 50 wt. % or less.

2. The emulsion of claim 1, wherein the emulsifier is from about 5.4 to about 8.5 wt %.

3. The emulsion of claim 1, wherein the dispersed phase is from about 8 to about 9 wt. %.

4. The emulsion of claim 1, wherein the water is from about 22 to about 24 wt. %.

5. The emulsion of claim 1, wherein the co-solvent is from about 14 to about 16 wt. %.

6. The emulsion of claim 1, wherein the mono-saccharide and/or di-saccharide is from about 44 to about 49 wt. %.

7. The emulsion of claim 1, wherein the ratio of the emulsifier to the dispersed phase is from about 1 to about 0.5.

8. The emulsion of claim 1, wherein the ratio of the emulsifier to the dispersed phase is from about 1 to about 0.7.

9. The emulsion of claim 1, wherein the combined amount of water and co-solvent is from about 30 to about 50 wt. %.

10. The emulsion of claim 1, wherein the total amount of water and co-solvent is from about 36 to about 40 wt. %.

11. The emulsion of claim 1, wherein the emulsifier comprises tocopherol polyethylene glycol succinate (TPGS) or an analog thereof.

12. The emulsion of claim 1, wherein the emulsifier comprises a polyethylene glycol-derivative of vitamin A, Retinol, Vitamin D1, Vitamin D2, Vitamin D3, Vitamin D4, Vitamin D5, Vitamin E, or a combination thereof.

13. The emulsion of claim 1, wherein the emulsifier comprises tocopherol polyethylene glycol diesters (TPGD) or an analog thereof, tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methyl citraconate polyethylene glycol, tocopherol itaconate polyethylene glycol, tocopherol maleate polyethylene glycol, tocopherol glutarate polyethylene glycol, tocopherol glutaconate polyethylene glycol, tocopherol phthalate polyethylene glycol, or polyoxyethanyl tocotrienyl sebacate.

14. The emulsion of claim 1, further comprising an antioxidant.

15. The emulsion of claim 1, wherein the dispersed phase comprises marine oil, a microbial oil, or an oil derived from a plant.

16. The emulsion of claim 1, wherein the dispersed phase comprises eicosapentaenoic acid (EPA), docosahexaenoic acid (DHA), eicosatetraenoic acid (AA), octadecatrienoic acid (GLA), octadecadienoic acid (LA) and/or docosapentaenoic acid (DPA), alkyl esters thereof, glyceride esters thereof, salts thereof, or any combination thereof.

17. The emulsion of claim 1, wherein the co-solvent comprises propylene glycol, glycerol, or a mixture thereof.

18. The emulsion of claim 1, wherein the disaccharide is present and comprises sucrose.

19. The emulsion of claim 1, wherein the emulsion is substantially free of a gum, benzyl alcohol, and/or phosphatidylcholine.

20. The emulsion of claim 1, wherein the emulsion comprises glucose, fructose, galactose, arabinose, ribose, ribulose, xylose, mannose, xylulose, sucrose, lactose, cellobiose, sorbose, trehalose, maltose, raffinose, xylitol, sorbitol, isomalt, or a combination thereof.

21. The emulsion of claim 1, wherein the hydrophilic-lipophilic balance (HLB) of the emulsifier is from about 12 to about 14.

22. The emulsion of claim 1, wherein the emulsion has an absorbance at 400 nm of less than about 0.3 A.

23. The emulsion of claim 1, wherein the emulsion has an absorbance at 400 nm of less than about 0.1 A.

24. The emulsion of claim 1, wherein the emulsion has droplet size of about 100 nm or less.

25. A beverage comprising the emulsion of claim 1.

26. A method for producing an emulsion comprising:
   a. emulsifying a mixture, comprising:
      i. from about 4 to about 15 wt. % of a polyethylene glycol derivative of a fat-soluble vitamin emulsifier;
      ii. from about 5 to about 10 wt. % of a dispersed phase; and
      iii. from about 5 to about 18 wt. % of a co-solvent;
   wherein the ratio of the emulsifier to the dispersed phase is about 1.5 or less;
   b. combining the emulsion from step a with a solution comprising:
      i. from about 20 to about 25 wt. % of water; and
      ii. from about 40 to about 55 wt. % of a mono-saccharide, a di-saccharide or both;
   wherein the combined amount of water and co-solvent is 50 wt. % or less; and
   c. homogenizing the mixture of step b by high pressure homogenization.

27. The method of claim 26, wherein the homogenization step is conducted at from 1500 to about 6000 psi.

28. The method of claim 26, wherein the emulsifier is from about 5.4 to about 8.5 wt %.

29. The method of claim 26, wherein the dispersed phase is from about 8 to about 9 wt. %.

30. The method of claim 26, wherein the water is from about 22 to about 24 wt. %.

31. The method of claim 26, wherein the co-solvent is from about 14 to about 16 wt. %.

32. The method of claim 26, wherein the mono-saccharide and/or di-saccharide is from about 44 to about 49 wt. %.

33. The method of claim 26, wherein the ratio of the emulsifier to the dispersed phase is from about 1 to about 0.5.

34. The method of claim 26, wherein the ratio of the emulsifier to the dispersed phase is from about 1 to about 0.7.

35. The method of claim 26, wherein the combined amount of water and co-solvent is from about 30 to about 50 wt. %.

36. The method of claim 26, wherein the total amount of water and co-solvent is from about 36 to about 40 wt. %.

37. The method of claim 26, wherein the emulsifier comprises tocopherol polyethylene glycol succinate (TPGS) or an analog thereof.

38. The method of claim 26, wherein the emulsifier comprises a polyethylene glycol derivative of Vitamin A, Retinol, Vitamin D1, Vitamin D2, Vitamin D3, Vitamin D4, Vitamin D5, Vitamin E, or a combination thereof.

39. The method of claim 26, wherein the dispersed phase comprises a marine oil, microbial oil, or algal oil.

40. The method of claim 26, wherein the dispersed phase comprises eicosapentaenoic acid (EPA), docosahexaenoic acid (DHA), eicosatetraenoic acid (AA), octadecatrienoic acid (GLA), octadecadienoic acid (LA) and/or docosapentaenoic acid (DPA), alkyl esters thereof, glyceride esters thereof, salts thereof, or any combination thereof.

41. The method of claim 26, wherein the co-solvent comprises propylene glycol, glycerol, or a mixture thereof.

42. The method of claim 26, wherein the disaccharide is present and comprises sucrose.

43. The method of claim 26, wherein the emulsion is substantially free of a gum, benzyl alcohol, and/or phosphatidylcholine.

44. The method of claim 26, further comprising an antioxidant.

45. The method of claim 26, wherein the emulsion comprises glucose, fructose, galactose, arabinose, ribose, ribulose, xylose, mannose, xylulose, sucrose, lactose, cellobiose, sorbose, trehalose, maltose, raffinose, xylitol, sorbitol, isomalt, or a combination thereof.

46. The method of claim 26, wherein the emulsion has an absorbance at 400 nm of less than about 0.3 A.

47. The method of claim 26, wherein the emulsion has an absorbance at 400 nm of less than about 0.1 A.

48. The method of claim 26, wherein the emulsion has droplet size of about 100 nm or less.

49. The method of claim 26, further comprising diluting the emulsion and the diluted emulsion maintains its clarity.

50. The method of claim 26, further comprising adding the emulsion into a beverage.

51. The method of claim 26, wherein the emulsifier comprises tocopherol polyethylene glycol diesters (TPGD) or an analog thereof, tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methyl citraconate polyethylene glycol, tocopherol itaconate polyethylene glycol, tocopherol maleate polyethylene glycol, tocopherol glutarate polyethylene glycol, tocopherol glutaconate polyethylene glycol, tocopherol phthalate polyethylene glycol, or polyoxyethanyl tocotrienyl sebacate.

52. The method of claim 26, wherein the hydrophilic-lipophilic balance (HLB) of the emulsifier is from about 12 to about 14.

\* \* \* \* \*